United States Patent
Keplinger

(10) Patent No.: US 8,932,623 B2
(45) Date of Patent: Jan. 13, 2015

(54) PROTECTIVE WOUND DRESSING DEVICE FOR ORAL AND PHARYNGEAL SPACE

(75) Inventor: Scott Alan Keplinger, Durham, NC (US)

(73) Assignee: Ethicon, Inc., Somerville, NJ (US)

( * ) Notice: Subject to any disclaimer, the term of this patent is extended or adjusted under 35 U.S.C. 154(b) by 264 days.

(21) Appl. No.: 13/217,852

(22) Filed: Aug. 25, 2011

(65) Prior Publication Data

US 2013/0052152 A1 Feb. 28, 2013

(51) Int. Cl.
| | |
|---|---|
| A61K 31/75 | (2006.01) |
| A61P 17/02 | (2006.01) |
| A61L 26/00 | (2006.01) |
| A61F 13/12 | (2006.01) |
| A61L 15/24 | (2006.01) |
| A61L 15/32 | (2006.01) |
| A61L 15/58 | (2006.01) |
| A61L 15/62 | (2006.01) |
| A61L 15/64 | (2006.01) |
| A61L 24/06 | (2006.01) |

(52) U.S. Cl.
CPC ........... *A61L 26/0052* (2013.01); *A61F 13/122* (2013.01); *A61L 15/24* (2013.01); *A61L 15/32* (2013.01); *A61L 15/58* (2013.01); *A61L 15/62* (2013.01); *A61L 15/64* (2013.01); *A61L 24/06* (2013.01); *A61L 26/0014* (2013.01); *A61L 26/0038* (2013.01); *A61L 2430/36* (2013.01)
USPC .......... 424/443; 424/78.18; 424/447

(58) Field of Classification Search
USPC ............................. 249/54; 602/46
See application file for complete search history.

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 3,995,641 A | 12/1976 | Kronenthal et al. | |
| 4,364,876 A | 12/1982 | Kimura et al. | |
| 4,524,064 A * | 6/1985 | Nambu ......................... | 424/445 |
| 5,328,687 A | 7/1994 | Leung et al. | |
| 5,658,592 A * | 8/1997 | Tanihara et al. .............. | 424/488 |
| 5,762,919 A * | 6/1998 | Greff et al. .................. | 424/78.17 |
| 5,928,611 A | 7/1999 | Leung | |
| 6,183,593 B1 | 2/2001 | Narang et al. | |
| 6,352,704 B1 | 3/2002 | Nicholson et al. | |
| 6,455,064 B1 | 9/2002 | Narang et al. | |
| 6,559,350 B1 | 5/2003 | Tetreault et al. | |
| 6,579,469 B1 | 6/2003 | Nicholson et al. | |
| 6,595,940 B1 | 7/2003 | D'3 Alessio et al. | |
| 6,620,846 B1 | 9/2003 | Jonn et al. | |
| 6,632,450 B1 | 10/2003 | Gregory | |
| 7,074,981 B2 * | 7/2006 | Chalmers ....................... | 602/41 |
| 2006/0251612 A1 | 11/2006 | Kotzev et al. | |
| 2011/0152924 A1 | 6/2011 | Gensini et al. | |

OTHER PUBLICATIONS

U.S. Appl. No. 11/704,115, filed Feb. 8, 2007.
U.S. Appl. No. 11/124,831, filed May 9, 2005.
U.S. Appl. No. 09/430,177, filed Oct. 29, 1999.
U.S. Appl. No. 09/919,877, filed Aug. 2, 2001.
U.S. Appl. No. 09/430,289, filed Oct. 29, 1999.
U.S. Appl. No. 09/385,030, filed Aug. 30, 1999.
U.S. Appl. No. 09/176,889, filed Oct. 22, 1998.
Gleeson, DC: Oropharyngeal swallowing and aging: a review; J. of Commun. Disorders;1999: vol. 32, pp. 373-395.
Ramjettan, S. et al.: Are sutured faucial pillars really an advantage in tonsillectomy?: South African J. of Surgery; 1996; vol. 34; pp. 189-191.
Reilly, JS et al.: Size/shape analysis of aerodigestive foreign bodies in children: A multi-institutional study; Am. J. of Otolaryngology; 1995; vol. 16; pp. 190-193.
Sclafani, AP et al.: Grafting of the peritonsillar fossa with an acellular dermal graft to reduce posttonsillectomy pain. Am J. Otolaryngol. 2001; vol. 22; pp. 409-414.

* cited by examiner

*Primary Examiner* — Walter Webb

(57) ABSTRACT

The present invention provides a wound dressing comprising a tessellated water-soluble molding matrix comprised of a polymer selected from the group consisting of polyvinyl alcohol, gelatin, and mixtures thereof and a 1,1-disubstituted ethylene monomer. The present invention further provides methods of using the wound dressing and kits containing the wound dressing.

15 Claims, 1 Drawing Sheet

PROTECTIVE WOUND DRESSING DEVICE FOR ORAL AND PHARYNGEAL SPACE

BACKGROUND OF THE INVENTION

The present invention relates to medical and surgical wound dressings and methods for making and using such dressings. In particular, the present invention relates to medical and surgical wound dressings where the wound dressing incorporates a water-soluble molding matrix to cause the resulting wound dressing to slough as particles of predictable maximum size and geometry. The medical and surgical wound dressings of the present invention provide a treatment to seal post-surgical sites of the oral and pharyngeal space that do not pose a choking hazard.

Approximately one million tonsillectomies, adenoidectomies, and tonsillectomy/adenoidectomy procedures combined were coded as surgical procedures in the United States in 2007. Although tonsillectomies and adenoidectomies are considered to be safe procedures, they still have significant morbidities of pain and postoperative bleeding. Post-operative pain causes great discomfort upon swallowing. In an attempt to avoid this pain, patients may experience dehydration and poor oral intake due to their lack of drinking and eating. The ideal treatment would alleviate pain without introducing additional safety risks such as choking.

After tonsillectomy, the risk of clinically significant aspiration of the "scab" appears to be near zero. It is not known whether the scab sloughs mostly intact or mostly in fragments. If it sloughs in fragments, fragment sizes are unknown. Route of elimination of the scab is unknown: coughing or swallowing? This lack of knowledge regarding the natural history of the tonsillectomy scab presents a challenge to the design of a protective wound dressing. It is desirable to create a dressing that reduces pain and reduces postoperative bleeding, but the dressing cannot cause complications such as choking, aspiration, or ingestion when the dressing is sloughed from the wound bed during healing.

Foreign body ingestion and aspiration are primarily pediatric problems. Since 1979 the United States has had regulations in effect which ban interstate commerce of any toy or other article intended for use by children under the age of three that presents a small parts choking hazard. There is a test fixture called a Small Parts Test Fixture used to determine if an object may cause a choking hazard for small children. The cylinder has a diameter of 31.7 mm and a depth of 25.4 to 57.2 mm (the cylinder has an angled top). The test method is described in 16 CFR Part 150: Method for Identifying Toys and Other Articles Intended for Use by Children Under 3 Years of Age Which Present Choking, Aspiration, or Ingestion Hazards Because of Small Parts. In a 1995 study of 534 incidents, 99% of aspirated foreign bodies would fail this test (Reilly J S et al, Size/shape analysis of aerodigestive foreign bodies in children: a multi-institutional study. *American Journal of Otolaryngology*. 1995; 16:190-193.). Nonetheless, the Small Parts Test Fixture is utilized in much of the world including Europe, the Americas, and China to prevent choking in children. In Reilly's study airway foreign bodies had an average length of 13.6 mm, width of 7.0 mm, and height of 5.7 mm. To not pose a choking hazard, it appears a fragment smaller than these dimensions is desirable.

A number of techniques have been evaluated for their ability to reduce the post-operative pain for these procedures. The Coblation Tonsillectomy procedure developed by ArthroCare Corporation (Austin, Tex.) was developed as a "less invasive" and thus less painful tonsillectomy method. This system utilizes radiofrequency to simultaneously ablate, resect, coagulate soft tissue, and provide hemostasis of blood vessels in a single device. Radiofrequency generates relatively low temperatures and reduces the amount of tissue damage. However, even with use of this surgical method, post-operative pain and bleeding are still significant morbidities.

Coverage of the post-surgical area has also been evaluated as a potential treatment for post-operative pain and bleeding. Grafting the peritonsillar fossa with an acellular dermal graft in a small study showed promise in pain reduction. However, the cost of this treatment is not commensurate with the reimbursement level for these surgical procedures. (Sclafani A P, Jacono A A, Dolitsky. Grafting of the peritonsillar fossa with an acellular dermal graft to reduce posttonsillectomy pain. *Am J. Otolaryngol.* 2001; 22:409-414.) In another study, the faucial pillar of the tonsil was sutured. This study showed no reduction in pain and, in fact, a greater complication rate. (Ramjettan S, Singh B. Are sutured faucial pillars really an advantage in tonsillectomy? *SATS* 1996; 34:189-191.)

Various biological and synthetic products have been evaluated as potential tonsillectomy dressings. These appear to suffer from a limited ability to adhere to the operative site (adherence), ability to hold together (cohesiveness), and/or ability to remain in place for a clinically relevant period (durability). As an example, fibrin sealants have been applied to the tonsillar fossa to help control post-operative bleeding and pain. Results reported in the literature regarding the effectiveness of this treatment have been mixed. Fibrin sealants lack the durability to protect the wound through the time of healing. The sealant sloughs off the site before full healing is achieved. Currently neither fibrin sealants nor any other product is approved or labeled by the Food and Drug Administration to control post-operative bleeding or pain in these specific procedures.

U.S. patent application Ser. No. 11/704,115, filed Feb. 8, 2007 by Hissong et al discloses use of a polymeric film-forming medical sealant for application to the tonsils and adenoids. The sealant performs at least one of the following functions a) inhibit the colonization of bacteria, b) inhibit the binding of bacteria to tissue, c) reduction of tissue morbidity, d) hemostasis, e) coating and protection of tissue during healing, and f) reduction of pain. Hissong et al discloses preferred polymeric film-forming medical sealants, but does not disclose how the polymeric film-forming medical sealant would slough from the tonsillectomy fossa.

U.S. Pat. No. 6,559,350 to Teterault et. al. discloses a moisture-curable adhesive suture strip for closing a wound on a patient. The suture strip is comprised of an air-permeable backing member formed of a chemically inert material, a moisture-curable surgical adhesive, and a removable protective member releasably secured to the backing member and covering the surgical adhesive. The backing member is formed of chemically inert materials such as polyethylene or tetrafluoroethylene. The backing member is described as having surface cavities filled with the surgical adhesive to anchor the backing member to the patient. Alternatively, the surgical adhesive may be applied as dots or stripes to the backing member. Based on the materials disclosed for the backing member, fragmentation is unlikely. The suture strip may slough more like a balloon and cause a greater choking hazard due to its conforming nature.

U.S. patent application Ser. No. 11/124,831, Filed May 9, 2005 by Kotzev et al discloses bioresorbable cyanoacrylate-based adhesives containing body fluid soluble additives. The body soluble additives are insoluble in cyanoacrylate monomer, but are readily dissolved out of the cured adhesive creating pores and channels for tissue ingrowth. The body soluble additives are used to facilitate resorption of the bulk material at a controllable resorption rate upon contact with a body fluid. As the body soluble additive are dispersed throughout the cyanoacrylate monomer, pores and channels are created as body fluids erode the bulk material. These pores and channels create random defects in the bulk material. When fragments are created their size is unpredictable.

Therefore, a need exists for a protective wound dressing that would help patients recover from tonsillectomy and adenoidectomy procedures. The post-operative treatment should fulfill several needs of the patient. This treatment must be both safe and effective. The treatment could be accomplished through the use of a protective wound dressing. Ideally, the wound dressing would act as a barrier and would protect tissue at and around the surgical site to make it easier and less painful for a patient to swallow. The wound dressing would adhere to post-surgical tissue and mucosal tissue even with the forces of swallowing and, in addition to reducing pain, would also reduce bleeding. Most importantly, the wound dressing sloughs from the tonsillar bed in predictable pieces during healing. By sloughing in this manner, the wound dressing does not pose a choking hazard.

BRIEF SUMMARY OF THE INVENTION

The present invention addresses the above needs in the art, and others, by providing improved materials and methods for treating a wound.

In an embodiment, the present invention provides a wound dressing comprising a tessellated water-soluble molding matrix comprised of a polymer selected from the group consisting of polyvinyl alcohol, gelatin, and mixtures thereof; and a 1,1-disubstituted ethylene monomer.

In another embodiment, the present invention provides a method of treating a wound comprising (1) (a) applying a 1,1-disubstituted monomer to a wound and embedding a tessellated water-soluble molding matrix comprised of a polymer selected from the group consisting of polyvinyl alcohol, gelatin, and mixtures thereof in said 1,1-disubstituted ethylene monomer, or (b) applying a tessellated water-soluble molding matrix comprised of a polymer selected from the group consisting of polyvinyl alcohol, gelatin, and mixtures thereof to a wound and applying a 1,1-disubstituted monomer to the wound filling at least a portion of at least one cell of the water-soluble molding matrix; (2) polymerizing the 1,1-disubstituted ethylene monomer; and (3) dissolving said water-soluble molding matrix leaving a molded polymer applied to said wound.

In another embodiment, the present invention provides a kit comprising at least one tessellated water-soluble molding matrix comprised of a polymer selected from the group consisting of polyvinyl alcohol, gelatin, and mixtures thereof; and at least one 1,1-disubstituted ethylene monomer.

BRIEF DESCRIPTION OF THE DRAWINGS

These and other advantages and features of this invention will be apparent from the following, especially when considered with the accompanying drawings, in which.

DETAILED DESCRIPTION OF THE INVENTION

Figure 1:
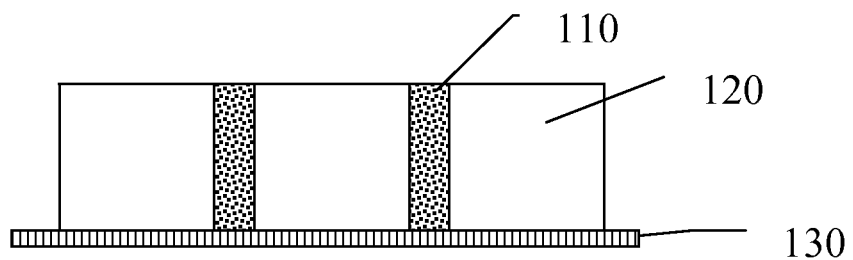
FIG. 1 illustrates use of one embodiment of the protective wound dressing device a wound.

The present invention addresses the above needs in the art, and others, by providing improved materials and methods for treating post-surgical sites in the oral and pharangeal space.

In embodiments, the materials and methods of the present invention provide significant advantages over the current materials and methods for treatment of post-surgical sites in the oral and pharangeal space. The materials and methods of the present invention provide a safe and effective protective wound dressing. Use of the protective wound dressing offers several benefits: reduction and/or elimination of post-operative pain, reduction of secondary post-operative bleeding, and a quicker return to normal activities for the patient. Most importantly, use of a water-soluble molding matrix according to the present invention creates a protective wound dressing that sloughs from the tonsillar bed in fragments of predictable size. Thus, the protective wound dressing of the present invention does not introduce an additional safety risk such as choking.

The protective wound dressing of the present invention is used as a covering for post-surgical sites in the oral and pharangeal space. The protective wound dressing is composed of two key elements: a water-soluble molding matrix and a 1,1-disubstituted ethylene monomer. The water-soluble molding matrix molds the 1,1-disubstituted ethylene monomer in situ into a configuration that sloughs off in predictable particle sizes of a maximum size, preventing a potential choking hazard.

These terms when used herein have the following meanings:

1. The term "water-soluble" as used herein, means soluble in water, saline or other body fluid such as saliva.
2. The term "fossa" as used herein, means a channel or shallow depression. A fossa is created when the tonsils are removed.
3. The term "polymerize" as used herein, means the process of the liquid monomeric material changing into a solid polymeric material. Polymerize, set, and cure are used interchangeably herein.
4. The term "biocompatible" means that the substance presents no significant deleterious or untoward effects upon the body.
5. The term "tessellation" or "tessellated" means a covering of a plane without gaps or overlappings by forms in a repeating pattern. The forms are polygons composed of straight or curved line segments. The forms may or may not be the same shape or the same size.

The wound dressing of the present invention is composed of two key elements: a water-soluble molding matrix and a 1,1-disubstituted ethylene monomer. The water-soluble molding matrix has the following features. It is constructed of a material that is water-soluble in water, saline, or other bodily fluids in a predictable timeframe. The water-soluble molding matrix is sizable to the surgical site geometry; it can be cut or manufactured to size. The water-soluble molding matrix pattern can take on any number of geometric configurations, with the cell configuration of the template determining the resultant polymerized adhesive particle maximum size and shape.

The water-soluble molding matrix is a cellular matrix that molds the 1,1-disubstituted ethylene monomer in situ into a configuration that sloughs off in predictable particle sizes of a maximum size. The water-soluble molding matrix utilizes a cellular structure to mold the adhesive. The water-soluble molding matrix has several additional features which are described in more detail below.

Most importantly, the water-soluble molding matrix is manufactured from a material that is water-soluble. The material must be water-soluble to mold the 1,1-disubstituted ethylene monomer in situ. Materials that are suitable for this purpose include gelatin and polyvinyl alcohol (PVOH). The water-soluble molding matrix may be formed from a combination of water-soluble materials. Material selection may be impacted by the selected water-soluble molding matrix configuration and/or the desired protective wound dressing application location. The material selection is easily determined by a person of ordinary skill in the art without undue experimentation.

The water-soluble molding matrix can be manufactured using a variety of processes including, but not limited to, solvent casting, injection molding, or punched from a polymeric sheet or film. The water-soluble molding matrix may be manufactured using a combination of processes. For example, a cellular pattern may be created using injection molding and be subsequently attached to a polymeric sheet or film using a secondary manufacturing process. The selection of manufacturing process will be dependent upon material selection and the configuration for the water-soluble molding matrix. The manufacturing process is easily determined by a person of ordinary skill in the art without undue experimentation.

The configuration of the cellular portion of the water-soluble molding matrix may be tessellated or random. Examples of tessellated patterns include polygon-based shapes such as triangular, rectangular, square, diamond, honeycomb, hexagonal, octagonal, fishscale or teardrop. An example of a random pattern might include a circular pattern that is punched into a film. In a given water-soluble molding matrix, the pattern may replicate the same shape, such as a pattern of squares that resembles a mesh; or the pattern may utilize multiple shapes, such as a hexagon surrounded by triangles that resembles a patchwork quilt.

The water-soluble molding matrix may have an open cell arrangement or a film-spanned configuration. In an open cell configuration, the cellular portion of the water-soluble molding matrix does not restrict flow of the 1,1-disubstituted ethylene monomer perpendicular to the wound upwards to fill the cells of the water-soluble molding matrix. The 1,1-disubstituted ethylene monomer can be applied to a wound first and the water-soluble molding matrix with an open cell arrangement placed on top of the 1,1-disubstituted ethylene monomer. The 1,1-disubstituted ethylene monomer will flow from the wound application upwards and into the cells of the water-soluble molding matrix prior to polymerization to form a wound dressing. The 1,1-disubstituted ethylene monomer will polymerize with the water-soluble molding matrix embedded in the polymer. Alternatively, a water-soluble molding matrix with an open cell arrangement can be placed on a wound first and a 1,1-disubstituted ethylene monomer applied to the wound through the cell of the water-soluble molding matrix. If the amount of 1,1-disubstituted ethylene monomer exceeds the volume of the water-soluble molding matrix, the 1,1-disubstituted ethylene monomer will overflow the matrix and encapsulate the matrix. If the matrix is encapsulated, it will not be exposed to water or saline and will not dissolve. To function as a protective wound dressing device, at least a portion of the water-soluble molding matrix must be exposed to water or saline in the polymerized dressing.

Preferably the water-soluble molding matrix has a film-spanned configuration. In a film-spanned configuration, the cellular portion of the water-soluble molding matrix is backed by a thin film. When using this type of water-soluble molding matrix, the 1,1-disubstituted ethylene monomer is applied to the wound first and the water-soluble molding matrix with a film-spanning configuration is applied over the adhesive prior to polymerization. The water-soluble molding matrix is applied to the wound with the cellular portion facing the 1,1-disubstituted ethylene monomer. The 1,1-disubstituted ethylene monomer will flow perpendicular to the wound upwards to fill the cells of the water-soluble molding matrix prior to polymerization of the 1,1-disubstituted ethylene monomer. If a volume of 1,1-disubstituted ethylene monomer is applied to the wound that exceeds the volume of the water-soluble molding matrix, the adhesive will create a continuous or semi-continuous layer of polymerized adhesive below the water-soluble molding matrix in the wound. It is preferred that this layer does not exceed about 10 mm.

Performance characteristics of the water-soluble molding matrix can be adjusted by pattern selection. For example, a water-soluble molding matrix that is based on an equilateral triangle 3 mm on a side and 3 mm deep will provide a different molded pattern in the polymerized composition than a water-soluble molding matrix that is based on a square 3 mm on a side and 3 mm deep. Performance characteristics may also be adjusted by sizing the water-soluble molding matrix characteristics. For example, a water-soluble molding matrix may be composed of a cellular pattern that is based on rectangles that are 2 mm wide by 4 mm long by 3 mm deep. A second water-soluble molding matrix with a deeper cellular pattern with rectangles that are 2 mm wide by 4 mm length by 5 mm deep will provide different performance characteristics. It is preferable to form fragments that are less than about 10 mm in any given dimension. It is more preferable to form fragments that are less than about 5 mm in any given dimension.

The water-soluble molding matrix remains in place preferably less than about 24 hours. More preferably, the water-soluble molding matrix remains in place less than about 12 hours. Most preferably, the water-soluble molding matrix remains in place less than about 8 hours. The time that the water-soluble molding matrix remains in place will depend upon several factors including material selection, configuration of the water-soluble molding matrix, and placement of the wound dressing. The desirable performance characteristics can be achieved by a person of ordinary skill in the art without undue experimentation.

The 1,1-disubstituted ethylene monomer has the following features. It is durable to withstand swallowing. It adheres to compromised tissue after a surgical procedure. It adheres to mucosal tissue. Preferred 1,1-disubstituted ethylene monomers are cyanoacrylates. The 1,1-disubstituted ethylene monomer may include one or more 1,1-disubstituted ethylene monomers, such as α-cyanoacrylates including, but not limited to, alkyl α-cyanoacrylates having an alkyl chain length of from about 1 to about 20 carbon atoms or more, preferably from about 3 to about 8 carbon atoms. Such monomers include those that form polymers, that may, but do not need to, biodegrade. Such monomers are disclosed in, for example, U.S. Pat. Nos. 5,328,687, 5,928,611 and 6,183,593, U.S. patent application Ser. No. 09/430,177, filed on Oct. 29, 1999, and U.S. Pat. No. 6,183,593, which are hereby incorporated in their entirety by reference herein. The α-cyanoacrylates of the present invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

Preferred α-cyanoacrylate monomers used in this invention include ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, or dodecylcyanoacrylate.

Other suitable cyanoacrylates for use in the present invention also include, but are not limited to, alkyl ester cyanoacrylate monomers. Such alkyl ester cyanoacrylates and other suitable monomers are disclosed in, for example, U.S. patent application Ser. No. 09/919,877, filed Aug. 2, 2001, and U.S. Pat. No. 6,620,846, the entire disclosures of which are incorporated herein by reference. Examples of preferred alkyl ester cyanoacrylates include, but are not limited to, butyl lactoyl cyanoacrylate, butyl glycoloyl cyanoacrylate, ethyl lactoyl cyanoacrylate, and ethyl glycoloyl cyanoacrylate.

The 1,1-disubstituted ethylene monomer may optionally also include at least one plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), dibutyl sebacate, polydimethylsiloxane, hexadimethylsilazane and others as listed in U.S. Pat. No. 6,183,593, the disclosure of which is incorporated in its entirety by reference herein.

In embodiments, the 1,1-disubstituted ethylene monomer may also include one or more polymerization initiators or rate modifiers. The polymerization initiator or rate modifier may be incorporated directly into the 1,1-disubstituted ethylene monomer. In such embodiments, the polymerization initiator or rate modifier is mixed with the 1,1-disubstituted ethylene monomer preferably immediately prior to or concurrent with application of the 1,1-disubstituted ethylene monomer to the wound. For example, the polymerization initiator or rate modifier and polymerizable adhesive composition can be mixed prior to application by suitable mixing devices in an applicator itself or in a separate container, or they can be mixed concurrent with application by mixing as the 1,1-disubstituted ethylene monomer is expressed from an applicator.

Suitable polymerization and/or cross-linking initiators and rate modifiers, and methods for applying them to substrates, are described in, for example, U.S. Pat. Nos. 5,928,611, 6,352,704, 6,455,064, 6,579,469 and 6,595,940 and U.S. patent application Ser. No. 09/430,177, filed Oct. 29, 1999, Ser. Nos. 09/430,289 09/430,180 filed Oct. 29, 1999; Ser. No. 09/385,030 filed Aug. 30, 1999; and Ser. No. 09/176,889 filed Oct. 22, 1998, the entire disclosures of which are incorporated herein by reference. Preferred initiators for some medical uses include benzalkonium chloride.

Particular initiators and rate modifiers for particular monomers may be readily selected by one of skill in the art without undue experimentation. Control of the molecular weight distribution of the applied adhesive can be enhanced by selection of the concentration and functionality of the initiator or rate modifier vis-a-vis the selected monomer. Suitable polymerization initiators and rate modifiers for cyanoacrylate compositions include, but are not limited to, detergent compositions; surfactants, including nonionic surfactants such as polysorbate 20 product (e.g., Tween 20™ product, ICI Americas), polysorbate 80 product (e.g., Tween 80™ product, ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin(II) 2-ethylhexanoate), and sodium tetradecyl sulfate; and amphoteric or zwitterionic surfactants such as dodecyldimethyl(3-sulfopropyl)ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; ascorbic acid; tannins and tannic acid; inorganic bases and salts, such as sodium bisulfate, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide.

In preferred embodiments, the initiator may be a bioactive material that possesses antiviral, antimicrobial, antifungal and/or wound healing properties. An example of such a material that possesses polymerization initiation and antiviral, antimicrobial, and/or antifungal properties is Gentian Violet, also known as crystal violet or methylrosaniline chloride. Examples of materials that possess polymerization initiation and wound healing properties also include various zinc complexes and zinc salts, antioxidants such as vitamin E and other vitamins and the like, and copper compounds such as copper chloride, copper sulfate and copper peptides. Such materials are particularly preferred because they can serve not only as the polymerization initiator or rate modifier for the cyanoacrylate monomer, they can also provide additional benefits to the wound site, such as antiviral effects, antimicrobial effects and/or antifungal effects or help to promote wound healing.

The polymerizable and/or cross-linkable material may also contain an initiator and/or a rate modifier which is inactive until activated by a catalyst or accelerator (included within the scope of the term "initiator" as used herein). Initiators activated by stimulation such as heat and/or light (e.g., ultraviolet or visible light) are also suitable if the flexible substrate is appropriately subjected to such stimulation. In addition to the polymerization and/or cross-linking initiator and/or rate modifier, the flexible substrate can also include various other materials that may or may not act as a polymerization initiator and/or rate modifier. For example, the flexible substrate can include a bioactive material, which may or may not also be a polymerization and/or cross-linking initiator and/or rate modifier. Examples of suitable bioactive materials include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof. Thus, in embodiments, the initiator and/or the rate modifier can be, but does not have to be, bioactive. In embodiments where the initiator and/or the rate modifier is bioactive, the method of the invention can be used to close, cover, or protect tissue and wounds while simultaneously providing a bioactive material to the tissue or wound.

Instead of being mixed with the 1,1-disubstituted ethylene monomer, the polymerization initiator or rate modifier may be incorporated directly into the water-soluble molding matrix during the manufacturing process. The initiator or rate modifier can be chemically bound, physically bound, absorbed, or adsorbed to the water-soluble molding matrix. In some cases, a polymerization initiator or rate modifier may not be needed at all.

The 1,1-disubstituted ethylene monomer may optionally also include thickeners. Suitable thickeners may include polymethylpethacrylate, poly(2-ethylhexy methacrylate), poly(2-ethylhexyl acrylate) and others as listed in U.S. Pat. No. 6,183,593, the disclosure of which is incorporated by reference herein in its entirety.

The 1,1-disubstituted ethylene monomer may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-microbial agents, such as, for example, various acidic anti-microbials, as identified above.

The 1,1-disubstituted ethylene monomer useful in the present invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference. Such preservatives can be in addition to any anti-microbial agent that may or may not be added to the composition. Such preservatives can be included irrespective of whether the composition and containers are sterilized.

The present invention may be used, among other things, to treat the tonsillar fossa created after a tonsillectomy procedure. The present invention may also be used to treat the gastrointestinal tract such as the esophagus or intestine. The present invention may also be used to treat the urinary bladder.

The method of treatment is described below. It is preferred that the wound dressing remain in place approximately 4 to 10 days, more preferably 4 to 8 days, most preferably 4 to 7 days.

1. If necessary, trim the water-soluble molding matrix to a size such that it will fit in the tonsillar fossa and cover all damaged tissue. Use of a water-soluble molding template with a film-spanned configuration is preferred.
2. Apply a 1,1-disubstituted ethylene monomer to the tonsillar fossa.
3. Place the water-soluble molding matrix over the 1,1-disubstituted ethylene monomer and press into the monomeric adhesive. Orient the water-soluble molding matrix such that the cellular side is embedded in the adhesive and the film side is covering the surface of the 1,1-disubstituted ethylene monomer.
4. Allow the 1,1-disubstituted ethylene monomer time to polymerize, embedding the cellular side of the water-soluble molding matrix in the polymerized adhesive.
5. Over time in situ, the water-soluble molding matrix dissolves and molds the polymerized wound dressing into the desired configuration.
6. As the polymerized wound dressing sloughs from the wound bed during the natural healing process, the pieces will fragment along the prescribed pathways created by the water-soluble molding matrix.

The present invention may be sold as a kit. The kit may be comprised of at least one water-soluble molding matrix and at least one 1,1-disubstituted ethylene monomer. The water-soluble molding matrices may be identical or different.

FIG. 1 illustrates one embodiment of the protective wound dressing of the present invention. To apply the protective wound dressing, the wound is first cleaned to remove any excess exudates, blood and to trim dead tissue. The wound is dried as much as possible. If the water-soluble molding matrix 110 is not sized for the wound, it is trimmed prior to use. The 1,1-disubstituted ethylene monomer 120 is applied to the wound 130. The water-soluble molding matrix 110 is pressed into the 1,1-disubstituted ethylene monomer 120 prior to polymerization. Alternatively, the water-soluble molding matrix 110 may be placed into the wound and the 1,1-disubstituted ethylene monomer 120 applied over the water-soluble molding matrix 110. After polymerization the water-soluble molding matrix 110 will dissolve when exposed to water or saline creating a protective wound dressing that sloughs off the wound in predictable particles sizes of a maximum size, preventing a potential choking hazard.

Figure 2:
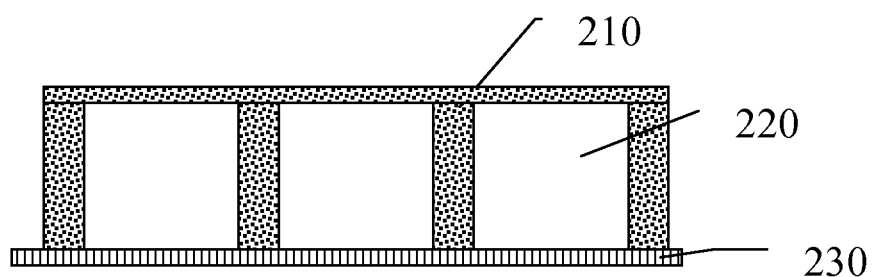
FIG. 2 illustrates use of a second embodiment of protective wound dressing device a wound.

FIG. 2 illustrates a second embodiment of the protective wound dressing of the present invention. To apply the protective wound dressing, the wound is first cleaned to remove any excess exudates, blood and to trim away dead tissue. The wound is dried as much as possible. If the water-soluble molding matrix 210 is not sized for the wound, it is trimmed prior to use. The composition 220 is applied to the wound 230. The water-soluble molding matrix 210 is pressed into the 1,1-disubstituted ethylene monomer 220 prior to polymerization. After polymerization the water-soluble molding matrix 110 will dissolve when exposed to water or saline creating a protective wound dressing that sloughs off the wound in predictable particles sizes of a maximum size, preventing a potential choking hazard.

The following examples are offered to illustrate embodiments of the invention, and should not be viewed as limiting the scope of the invention.

EXAMPLES

Example 1

Preparation of a Water-Soluble Molding Matrix with an Open Cell Configuration 28.35 grams of unflavored Knox® gelatin (Kraft Foods, Inc.) was added to a beaker containing 236.6 mL purified cold water. Approximately ten drops of green food coloring were added to the mixture to tint the resulting water-soluble molding matrix. The beaker was placed on a stir plate and heated to approximately 60° C. and the contents were stirred at a medium speed of agitation for approximately thirty minutes until all gelatin was in solution. While still at the elevated temperature, the solution was poured in a flexible silicone mold with dimensions of 100 mm by 100 mm with a cell of 10 mm by 10 mm and a cell depth of approximately 10 mm. The solution was poured into the flexible mold such that the solution filled the cell only and did not cover the entire mold surface. The silicone mold containing the solution was placed into a refrigerator for 24 hours. The resulting water-soluble molding matrix manufactured from gelatin was carefully removed from the silicon mold for use after the 24 hour time period.

Example 2

Preparation of a Water-Soluble Molding Matrix with a Film-Spanned Configuration 6 grams of polyvinyl alcohol powder (molecular weight approximately 20,000 Daltons, MP Biomedicals, LLC) was added to a beaker containing 60 mL of a 50/50 by volume mixture of isopropyl alcohol and purified water. Approximately five to six drops of red food coloring were added to the mixture to tint the resulting water-soluble molding matrix. The beaker was placed on a stir plate and heated to approximately 80° C. and the contents were stirred at a medium speed of agitation for approximately thirty minutes until all powder was in solution. While still at the elevated temperature, the solution was poured in a flexible silicone mold with dimensions of 150 mm by 150 mm with a cell of 5 mm by 5 mm and a cell depth of approximately 3 mm. The solution was poured into the flexible mold such that the solution filled the cell as well as a thin film layer over the entire cell area. The silicone mold containing the solution was placed into an incubator oven set to approximately 37° C. for 6 to 8 hours until the film solidified. The resulting water-soluble molding matrix manufactured from polyvinyl alcohol was carefully removed from the silicon mold for use after the 6 to 8 hour time period.

Example 3

Durability Evaluation of Wound Dressing Utilizing Example 1 Water-Soluble Molding Matrix A bench method was developed to evaluate samples produced according to the present invention. The test fixture was kept at approximately 37° C. to approximate body temperature. Samples were kept moist using saline to simulate saliva or other bodily fluids. Samples were subjected to an abrasive force generated by a roller to simulate swallowing. The average adult swallows 1000 times a day (Gleeson, D C. Oropharyngeal swallowing and aging: A review. *J. Commun. Disord.* 1999:32; 373-396). As a result, 500 cycles of the test apparatus (one back and forth motion) represents approximately one day. Since this abrasive force was much more aggressive than swallowing, these test results were considered a "worst case scenario".

A foam pad (McMaster-Carr) was placed onto the bed of an Elcometer 1720 Abrasion Tester to support the test sample. A piece of collagen (250 mm by 150 mm by ~5 mils, Vista International Packaging, LLC) was moistened with saline and affixed to the test apparatus over the foam pad. A pre-cut piece of the water-soluble molding matrix of Example 1 was placed down onto the center of the collagen matrix affixed to the test apparatus. A cyanoacrylate adhesive formulation (2-octyl cyanoacrylate, stabilizers, dye, and an initiator) was applied to the water-soluble molding matrix in the cells of the cell such that there was a thin film of adhesive completely covering the collagen substrate inside the cell area. The water-soluble molding matrix was held in place until the formulation polymerized.

The roller portion of the test fixture was attached to the carriage and a 200 gram weight was added. The cover frame was put into position. The reservoir bottle was filled with 0.9% saline solution (Baxter Healthcare, Inc.) and set to drip once or twice per cycle. A heat lamp was used to maintain a test sample temperature of approximately 37° C. The cycle rate speed setting was 4 (approximately 29 cycles per minute). The cycle count was set to 10,000.

A video camera was used to record the test sample during the durability evaluation. Table One details the results.

TABLE ONE

| Cycles | Observation |
| --- | --- |
| 0 | Full coverage of polymerized adhesive and gelatin matrix fully intact |
| 30 | ~50% gelatin water-soluble molding matrix dissolved, polymerized adhesive intact with some perforated matrix pattern embossed |
| 100 | ~80% gelatin water-soluble molding matrix dissolved, polymerized adhesive intact with perforated matrix pattern embossed |
| 300 | 100% gelatin water-soluble molding matrix dissolved, polymerized adhesive in clearly separated squares, when handled the polymerized adhesive breaks apart easily at embossed perforated cell lines |

Example 4

Durability Evaluation of Wound Dressing Utilizing Example 2 Water-Soluble Molding Matrix The testing described in Example 3 was conducted with the water-soluble molding matrix of Example 2 with some modifications.

The water-soluble molding matrix of Example 2 was cut into a circle with a diameter of approximately 30 mm. A cyanoacrylate adhesive formulation (2-octyl cyanoacrylate, stabilizers, dye, and an initiator) was applied to a latex sheet (250 mm by 150 mm by ~5 mils, McMaster-Carr) in a layer approximately 3 to 5 mm thick in a circle approximately 30 mm in diameter. While the formulation was still liquid, the water-soluble molding matrix was pressed into the formulation with the cellular portion facing the adhesive and the film facing upward. The water-soluble molding matrix was held in place until the formulation polymerized.

A foam pad (McMaster-Carr) was placed onto the bed of an Elcometer 1720 Abrasion Tester to support the test sample on the latex sheet. The roller test fixture was attached to the carriage and a 200 gram weight was added. The latex sheet containing the test sample was placed onto the bed of the fixture and the cover frame was put into position. The reservoir bottle was filled with 0.9% saline solution (Baxter Healthcare, Inc.) and set to drip once or twice per cycle. A heat lamp was used to maintain a test sample temperature of approximately 37° C. The cycle rate speed setting was 4 (approximately 29 cycles per minute). The cycle count was set to 10,000.

A video camera was used to record the test sample during the durability evaluation. Table Two details the results.

TABLE TWO

| Cycles | Observation |
| --- | --- |
| 0 | Test specimen fully intact, 100% coverage |
| 1800 | ~60% polyvinyl alcohol water-soluble molding matrix dissolved, polymerized adhesive intact with some perforated cell pattern embossed |
| 7700 | 100% polyvinyl alcohol water-soluble molding matrix dissolved, polymerized adhesive intact with perforated matrix pattern embossed |
| 10000 | Some polymerized adhesive squares have broken off the wound dressing, when handled the polymerized adhesive breaks apart easily at embossed perforated matrix lines |

While the invention has been described with reference to preferred embodiments, the invention is not limited to the specific examples given, and other embodiments and modifications can be made by those skilled in the art without departing from the spirit and scope of the invention.

The invention claimed is:

1. A wound dressing comprising:
   A) a tessellated water-soluble molding matrix comprised of a polymer selected from the group consisting of polyvinyl alcohol, gelatin, and mixtures thereof; and
   B) a 1,1-disubstituted ethylene monomer.

2. The wound dressing of claim 1 wherein said 1,1-disubstituted ethylene monomer comprises a cyanoacrylate.

3. The wound dressing of claim 2 wherein said cyanoacrylate is selected from the group consisting of ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, butyl lactoyl cyanoacrylate, butyl glycolcyl cyanoacrylate, ethyl lactoyl cyanoacrylate, and ethyl glycoloyl cyanoacrylate.

4. The wound dressing of claim 1 wherein the tessellated water-soluble molding matrix is comprised of cells measuring less than about 5 mm in any given dimension.

5. The wound dressing of claim 1 wherein the tessellated water-soluble molding matrix is comprised of cells measuring less than about 3 mm in any given dimension.

6. A method of treating a wound comprising:
   (1) (a) applying a 1,1-disubstituted monomer to a wound and embedding a tessellated water-soluble molding matrix comprised of a polymer selected from the group consisting of polyvinyl alcohol, gelatin, and mixtures thereof in said 1,1-disubstituted ethylene monomer, or
   (b) applying a tessellated water-soluble molding matrix comprised of a polymer selected from the group consisting of polyvinyl alcohol, gelatin, and mixtures thereof to a wound and applying a 1,1-disubstituted monomer to the wound filling at least a portion of at least one cell of the water-soluble molding matrix;
   (2) polymerizing the 1,1-disubstituted ethylene monomer; and
   (3) dissolving said water-soluble molding matrix leaving a molded polymer applied to said wound.

7. The method of claim 6 wherein said 1,1-disubstituted ethylene monomer comprises a cyanoacrylate.

8. The method of claim 7 wherein said cyanoacrylate is selected from the group consisting of ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, butyl lactoyl cyanoacrylate, butyl glycolcyl cyanoacrylate, ethyl lactoyl cyanoacrylate, and ethyl glycoloyl cyanoacrylate.

9. The method of claim 6 wherein the tessellated water-soluble molding matrix is comprised of cells measuring less than about 5 mm in any given dimension.

10. The wound dressing of claim 6 wherein the tessellated water-soluble molding matrix is comprised of cells measuring less than about 3 mm in any given dimension.

11. A kit comprising:
    A) at least one tessellated water-soluble molding matrix comprised of a polymer selected from the group consisting of polyvinyl alcohol, gelatin, and mixtures thereof; and
    B) at least one 1,1-disubstituted ethylene monomer.

12. The kit of claim 11 wherein said 1,1-disubstituted ethylene monomer comprises a cyanoacrylate.

13. The kit of claim 12 wherein said cyanoacrylate is selected from the group consisting of ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, butyl lactoyl cyanoacrylate, butyl glycolcyl cyanoacrylate, ethyl lactoyl cyanoacrylate, and ethyl glycoloyl cyanoacrylate.

14. The kit of claim 11 wherein the tessellated water-soluble molding matrix is comprised of cells measuring less than about 5 mm in any given dimension.

15. The kit of claim 11 wherein the tessellated water-soluble molding matrix is comprised of cells measuring less than about 3 mm in any given dimension.

* * * * *